US009974442B2

(12) United States Patent
Plakas et al.

(10) Patent No.: US 9,974,442 B2
(45) Date of Patent: May 22, 2018

(54) METHOD OF, AND APPARATUS FOR, PROCESSING VOLUMETRIC IMAGE DATA

(71) Applicant: TOSHIBA MEDICAL SYSTEMS CORPORATION, Otawara-Shi (JP)

(72) Inventors: Costas Plakas, Edinburgh (GB); Brian Mohr, Edinburgh (GB); Saad Masood, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 795 days.

(21) Appl. No.: 13/925,121

(22) Filed: Jun. 24, 2013

(65) Prior Publication Data

US 2014/0378850 A1 Dec. 25, 2014

(51) Int. Cl.
*A61B 5/02* (2006.01)
*A61B 5/026* (2006.01)
(Continued)

(52) U.S. Cl.
CPC .......... *A61B 5/02007* (2013.01); *A61B 5/026* (2013.01); *A61B 5/7275* (2013.01);
(Continued)

(58) Field of Classification Search
CPC ... A61B 5/026; A61B 5/02007; A61B 5/7275; G06T 7/0012; G06T 2207/10088;
(Continued)

(56) References Cited

U.S. PATENT DOCUMENTS

| 5,872,861 | A | 2/1999 | Makram-Ebeid |
| 8,498,462 | B2 * | 7/2013 | Niinuma ............... G06T 7/0012 |
| | | | 382/130 |

(Continued)

FOREIGN PATENT DOCUMENTS

| CN | 102207991 A | 10/2011 |
| JP | 5-264232 | 10/1993 |

(Continued)

OTHER PUBLICATIONS

Combined Office Action and Search Report dated Dec. 25, 2015 in Chinese Patent Application No. 201410285921.7 with English translation of category of cited documents.

(Continued)

*Primary Examiner* — Meredith Weare
(74) *Attorney, Agent, or Firm* — Oblon, McClelland, Maier & Neustadt, L.L.P.

(57) ABSTRACT

An apparatus for processing volumetric image data to identify vessel regions having a predetermined condition, comprises a measurement unit for measuring at least one vessel parameter, a reference identification unit for obtaining data representing a branch-free vessel and identifying at least one reference section of the branch-free vessel, a calculation unit for calculating an expected value of the parameter in a further section of the branch-free vessel based on at least one measured value of the parameter in the at least one reference section, and a region identification unit for identifying a region of the vessel having the predetermined condition in dependence on both the expected value of the parameter in the further section and a measured value of the parameter in the further section.

21 Claims, 4 Drawing Sheets

(51) Int. Cl.
*A61B 5/00* (2006.01)
*G06T 7/00* (2017.01)

(52) U.S. Cl.
CPC .. *G06T 7/0012* (2013.01); *G06T 2207/10081* (2013.01); *G06T 2207/10088* (2013.01); *G06T 2207/30101* (2013.01); *G06T 2207/30172* (2013.01)

(58) Field of Classification Search
CPC . G06T 2207/30172; G06T 2207/30101; G06T 2207/10081
See application file for complete search history.

(56) References Cited

U.S. PATENT DOCUMENTS

| | | | | |
|---|---|---|---|---|
| 8,526,699 | B2* | 9/2013 | Mittal | G06T 7/0016 382/131 |
| 8,582,844 | B2* | 11/2013 | Nakayama | A61B 6/481 382/128 |
| 2003/0171894 | A1 | 9/2003 | Mancini et al. | |
| 2004/0249270 | A1* | 12/2004 | Kondo | G06T 15/08 600/425 |
| 2005/0010100 | A1 | 1/2005 | Hornegger et al. | |
| 2005/0180621 | A1* | 8/2005 | Raman | A61B 5/02007 382/128 |
| 2006/0056685 | A1* | 3/2006 | Kiraly | G06T 7/0012 382/165 |
| 2006/0079746 | A1 | 4/2006 | Perret et al. | |
| 2007/0244393 | A1* | 10/2007 | Oshiki | A61B 5/02007 600/463 |
| 2008/0118131 | A1* | 5/2008 | Skinner | G06T 7/0012 382/131 |
| 2008/0122842 | A1* | 5/2008 | Sirohey | G06K 9/34 345/424 |
| 2009/0268954 | A1* | 10/2009 | Niinuma | G06T 7/0012 382/128 |
| 2010/0076296 | A1* | 3/2010 | Mittal | G06T 7/0012 600/408 |
| 2010/0128963 | A1* | 5/2010 | Waku | A61B 5/0073 382/134 |
| 2011/0096964 | A1* | 4/2011 | Zheng | G06T 7/0048 382/128 |
| 2011/0190626 | A1 | 8/2011 | Mizuno | |
| 2011/0224542 | A1* | 9/2011 | Mittal | G06T 7/0016 600/425 |
| 2011/0235878 | A1* | 9/2011 | Nakayama | A61B 6/481 382/128 |
| 2013/0066197 | A1* | 3/2013 | Pruvot | G06T 7/0012 600/427 |
| 2013/0158970 | A1 | 6/2013 | Hof et al. | |

FOREIGN PATENT DOCUMENTS

| | | |
|---|---|---|
| JP | 2004-283583 | 10/2004 |
| JP | 2005-0198708 | 7/2005 |
| JP | 2006-110341 | 4/2006 |
| JP | 2007-506531 | 3/2007 |
| JP | 2008-79682 | 4/2008 |
| JP | 2009-0261651 | 11/2009 |
| JP | 2012-0081254 | 4/2012 |
| WO | WO 2010/055815 A1 | 5/2010 |
| WO | WO 2010055815 A1 * | 5/2010 ............. A61B 6/481 |

OTHER PUBLICATIONS

P. M. Rothwell, et al., "Equivalence of measurements of carotid stenosis. A Comparison of three methods on 1001 angiograms. European Carotid Surgery Trialists' Collaborative Group.", Stroke 25, 1994, 6 pages.

Office Action dated Feb. 13, 2018, in Japanese Patent Application No. 2014-118150, citing documents AO, AP, and AQ therein, 93 pages.

* cited by examiner

METHOD OF, AND APPARATUS FOR, PROCESSING VOLUMETRIC IMAGE DATA

FIELD

Embodiments described herein relate generally to a method of, and apparatus for, processing volumetric image data to identify vessel regions having a predetermined condition. Embodiments have particular application to the identification and quantification of stenosis in arteries.

BACKGROUND

It is well known to use medical imaging techniques to obtain image data that is representative of structures within the body of a patient or other subject. It is known to perform angiography to image the blood vessels.

Traditionally, angiography has been in the form of catheter angiography, in which a catheter is inserted into a large vessel and navigated to the point of interest (for example, the heart), where a contrast agent is injected and multiple two-dimensional still images or short films are taken using X-ray fluoroscopy. In these images, the vessels may be seen clearly due to the contrast agent. Catheter angiography is an invasive process.

An alternative to catheter angiography is CT (computerized tomography) angiography. In CT angiography, a contrast agent is introduced into a blood vessel and a CT scan is then taken, in which multiple slices are combined to provide a three-dimensional image data set, with blood vessels highlighted by the contrast agent. CT angiography is considered one of the best tools to non-invasively analyze vessels for structural problems.

Other modalities of imaging are also possible, with or without the use of a contrast agent.

One form of structural problem that occurs in blood vessels is the formation of stenoses. A stenosis is an abnormal constriction or narrowing of a vessel. FIG. 1 is an image of a blood vessel showing two normal vessel regions 2 and two regions of stenosis 4. The regions of stenosis can be seen as narrowed sections of the vessel. Stenosis can manifest in different anatomical parts, for example coronary artery stenosis, renal artery stenosis or carotid artery stenosis.

It may be possible to manually identify stenoses on medical images of the blood vessels, assuming that a suitable view may be found in which the stenosis is apparent. However, it can be time-consuming and cumbersome. Choosing angles and measurement views is not straightforward, as visibility of the vessels and the ability to assess narrowing will change with angle. Additionally, manual identification and quantification can produce measurement results that are dependent on the user.

There exist methods that identify stenosis automatically within a given vessel section, but such methods are often complex and in some cases also require manual identification of the relevant vessel section by a user.

BRIEF DESCRIPTION OF THE DRAWINGS

Embodiments are now described, by way of non-limiting example, and are illustrated in the following figures, in which.

DETAILED DESCRIPTION

Certain embodiments provide an apparatus for processing volumetric image data to identify vessel regions having a predetermined condition, comprising, a measurement unit for measuring at least one vessel parameter, a reference identification unit for obtaining data representing a branch-free vessel and identifying at least one reference section of the branch-free vessel, a calculation unit for calculating an expected value of the parameter in a further section of the vessel based on at least one measured value of the parameter in the at least one reference section, and a region identification unit for identifying at least one vessel region having the predetermined condition in dependence on both the expected value of the parameter in the further section and a measured value of the parameter in the further section.

Certain embodiments provide a method for automatic detection of vessel regions having a condition, comprising obtaining data representing a branch-free vessel, identifying at least one reference section of the branch-free vessel, measuring at least one value of a parameter for the at least one reference section, measuring a value of the parameter in a further section of the vessel, calculating an expected value of the parameter in the further section of the vessel based on the at least one measured value for the at least one reference section, and identifying a vessel region having the condition in dependence on a comparison between the expected value of the parameter in the further section and the measured value of the parameter in the further section.

Figure 1:
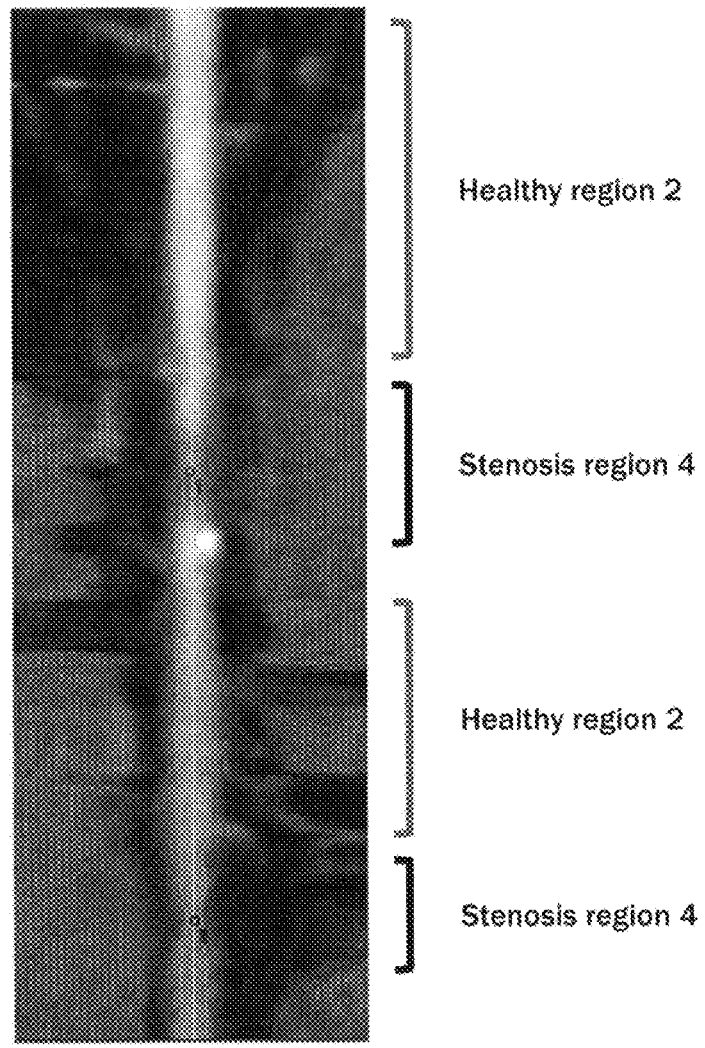
FIG. 1 is an image of a blood vessel comprising healthy regions and regions of stenosis.
Figure 2:
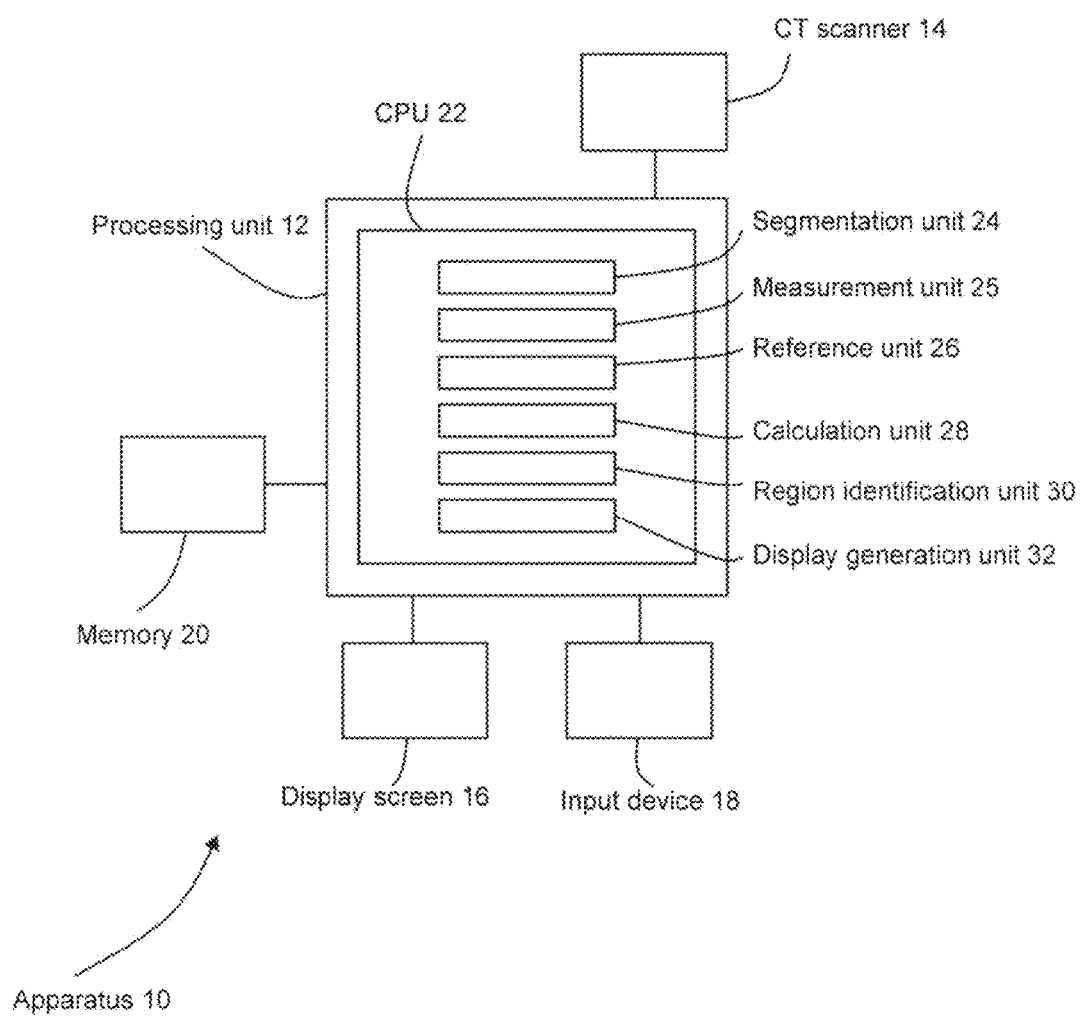
FIG. 2 is a schematic illustration of an apparatus according to an embodiment.

An apparatus 10 according to an embodiment is illustrated schematically in FIG. 2. In this embodiment, the predetermined condition is stenosis and the parameter is the lumen diameter of the vessel.

The apparatus 10 comprises a processing apparatus 12, in this case a personal computer (PC) or workstation, that is connected to a CT scanner 14, a display screen 16 and an input device or devices 18, such as a computer keyboard and mouse. In this embodiment, the CT scanner 14 is one of the Toshiba Aquilion (RTM) range of CT scanners. It may instead be any CT scanner that is configured to obtain three-dimensional image data, or a scanner that supports another modality of imaging, for example, an MRI scanner.

In this embodiment, sets of image data obtained by CT scanner 14 are stored in memory 20 and subsequently provided to processing apparatus 12. In an alternative embodiment, sets of image data are supplied from a remote data store (not shown) which may form part of a Picture Archiving and Communication System (PACS). The memory 20 or remote data store may comprise any suitable form of memory storage.

The processing apparatus 12 provides a processing resource for automatically or semi-automatically processing sets of image data. It comprises a central processing unit (CPU) 22 that is operable to load and execute a variety of software modules or other software components that are configured to perform the method that is described below with reference to FIG. 3.

The processing apparatus 12 includes a measurement unit 25 for measuring a parameter of the vessel, a reference identification unit 26 for identifying reference sections of vessels from the volumetric image data, a calculation unit 28 for calculating expected values for the parameter in at least one further section, and a region identification unit 30 for identifying regions having the predetermined condition (in this embodiment, stenosis regions) and determining a measure of severity of the condition (in this case, the percentage stenosis at the maximum stenosis point).

In this embodiment, the processing apparatus 12 also includes a segmentation unit 24 for extracting a vessel tree from the set of image data, and a display generation unit 32 for generating an image derived from the set of image data for display on display screen 16, in which the region or regions having the predetermined condition (in this case, stenosis regions) are highlighted. The vessel tree may be extracted manually or automatically in various embodiments, and in some cases may be pre-extracted and read when needed.

In this embodiment, the measurement unit 25, reference identification unit 26, calculation unit 28, region identification unit 30, segmentation unit 24 and display generation unit 32 are each implemented in the processing apparatus 12 by means of a computer program having computer-readable instructions that are executable to perform the method of the embodiment. However, in other embodiments, each unit may be implemented in software, in hardware, or in any suitable combination of hardware and software. In some embodiments, the various units may be implemented as one or more ASICs (application specific integrated circuits). In further embodiments, one or more units may be implemented on a GPU (graphics processing unit).

The processing apparatus 12 also includes a hard drive and other components of a PC including RAM, ROM, a data bus, an operating system including various device drivers, and hardware devices including a graphics card. Such components are not shown in FIG. 2 for clarity.

Figure 3:
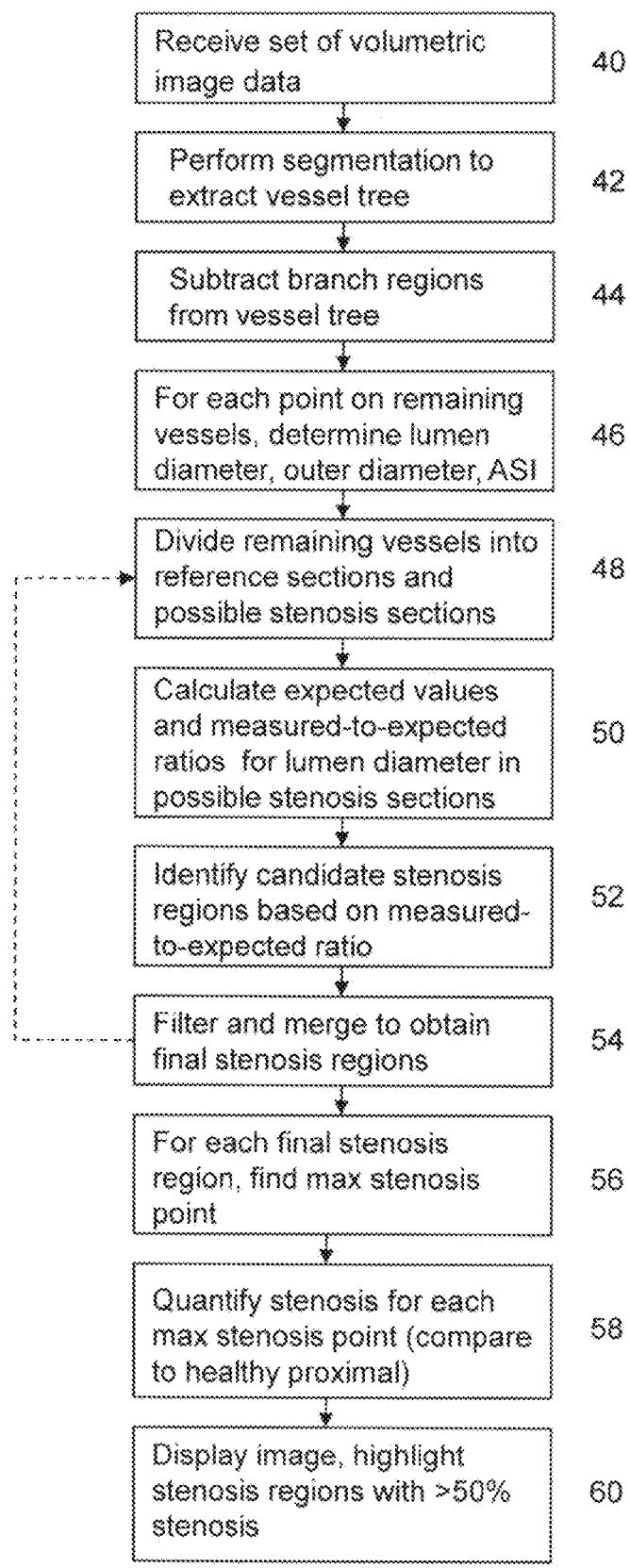
FIG. 3 is a flow chart illustrating in overview a process performed in accordance with an embodiment.

The system of FIG. 2 is configured to perform a process having a sequence of stages as illustrated in overview in the flow chart of FIG. 3.

In the embodiment of FIG. 3, the coronary arteries are assessed for stenosis. In further embodiments, the vessels assessed for stenosis may be any part of the vascular system, for example renal arteries or carotid arteries.

Firstly, at stage 40, the segmentation unit 24 receives a set of image data from the memory 20 or from a remote data store. In this embodiment, the set of image data is a set of three-dimensional data relating to the heart region of a patient, obtained by coronary CT angiography using CT scanner 14. The process of FIG. 3 may be performed in real-time (during or immediately after the CT scan) or on previously-taken CT data.

At stage 42, the segmentation unit 24 performs segmentation of the set of volumetric image data using any suitable known segmentation method (for example, any one or more of region growing based segmentation, active contours, intensity and shape classification based segmentation) to isolate the parts of the image data that represent the blood vessels of interest (in this embodiment, a vessel tree comprising the coronary arteries). In alternative embodiments, segmentation is performed manually.

In this embodiment, the segmentation unit 24 identifies branch points in the segmented tree representation. The segmentation unit may identify branch points by any suitable method, for example by tracking the vessel center line for each vessel and identifying where center lines intersect.

In further embodiments, the set of volumetric image data supplied from the memory 20 or remote data store has already been segmented to extract the vessel tree before being added to the memory 20 or remote data store. In this case, the segmented set of volumetric image data is supplied directly to the reference identification unit 26 and no segmentation unit 24 is required in processing unit 12. This segmented set of data may comprise the branch points.

At stage 44, the reference identification unit 26 receives the segmented set of volumetric image data representing the vessel tree comprising the coronary arteries from the segmentation unit 24, memory 20 or remote data store The set of volumetric image data includes a representation of the vessel tree in which the branch points are identified. For each branch point, the reference identification unit 26 defines a branch region, which comprises the branch point and a small section of each of the vessels that meet at the branch point. The extent of the branch region is defined by a branch threshold length. This determines the length of the part of each vessel that is included in the branch region. In this embodiment, the branch threshold length is 1 mm and is set as a fixed setting in the reference identification unit 26. The branch region thus comprises the branch point and a 1 mm length of each vessel that meets at the branch point, measured from the branch point itself. In other embodiments, a different branch threshold length setting is used. In alternative embodiments, the reference identification unit 26 determines a branch threshold length by any appropriate automatic method.

In further embodiments, the branch threshold length is input by a user before step 44, for example by using input device 18, and the user input is received by the reference identification unit 26. The user may input a branch threshold length to be used for one specific instance of the process described in FIG. 3. Alternatively, the user may input a branch threshold length to be used in all processes, or one or more branch threshold lengths to be used in specified processes (for example, the user may input a different value of branch threshold length for coronary artery assessment than for renal artery assessment, or a different value for CT data than for MRI data). The branch threshold length may apply to all branch points in the vessel tree, or may be different for different branch points.

Figure 4A:
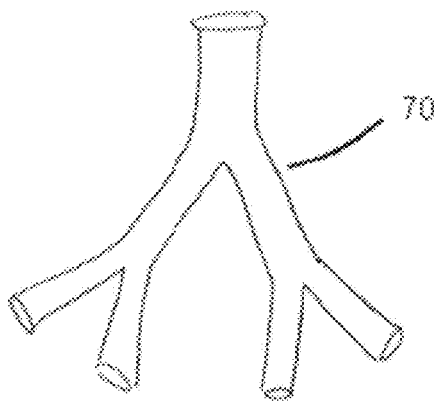
FIGS. 4a, 4b and 4c are schematic diagrams illustrating the removal of branch regions from a vessel tree.
Figure 4B:
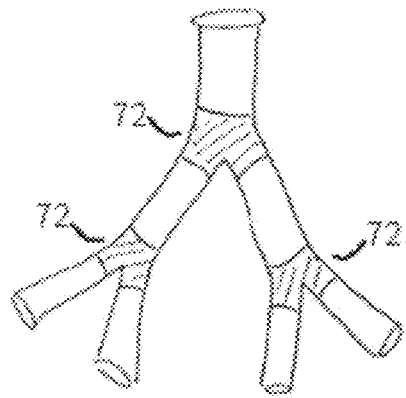
Figure 4C:
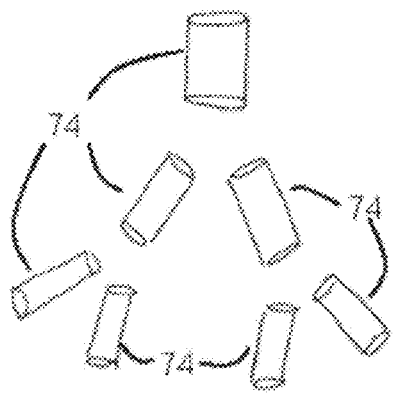

In other embodiments, the reference identification unit 26 determines a branch threshold length. A single branch threshold length may apply to all branch points, or a different branch threshold length may apply to different branch points. The branch threshold length may be dependent on the process in question or on the details of the data or parameters of the vessel tree. Once branch regions have been identified, the region identification unit 26 removes the branch regions from the vessel tree under consideration, leaving only unbranched sections of vessels. FIGS. 4a, 4b and 4c are schematic diagrams representing the process of branch region removal. FIG. 4a shows a vessel tree 70 comprising three branch points. FIG. 4b shows the vessel tree 70 with three branch regions 72 marked by shading. FIG. 4c shows the resulting unbranched vessel sections 74 after removal of the branch regions. It should be noted that these diagrams are not to scale and are merely schematic representations of a vessel tree. In particular, the extent of each branch region 72 is exaggerated compared to the length of the unbranched vessel sections 74. It should also be noted that although these diagrams represent the removal of branch regions as if this process were carried out on an image of the vessel tree, the branch region removal process is performed on the set of volumetric image data comprising segmented blood vessels that was provided by the segmentation unit 24, memory 20 or remote data store, and does not necessarily comprise the creation of an image. Removal of the branch regions may comprise removing data from the data set, or may alternatively comprise not considering the branch region data in further steps of the process. It may comprise flagging the data so that it is not used in further processing, creating a second or further data set from the original data set, or any other suitable process.

Once the reference identification unit 26 removes the branch regions 72, the remaining parts of the vessel tree may comprise several unbranched vessel sections 74 as represented in FIG. 4c. The process of assessing stenosis in one of these unbranched vessel sections 74 is discussed below with reference to the flow chart of FIG. 3. This process is performed on each of the unbranched vessel sections 74 that results from the removal of branch regions 72 at stage 44.

At stage 46, for each unbranched vessel section 74, the measurement unit 25 selects a series of points along the length of the unbranched vessel section 74 and measures at each point a lumen size parameter, in this case a lumen diameter (inner diameter of the vessel), and a vessel size parameter, in this case an outer diameter of the vessel.

Firstly, the measurement unit 25 determines the position of the centerline of the vessel at each of the series of points, using any suitable known method. For example, in one embodiment a vessel centerline is tracked between two provided points with some minimum cost. In an alternative embodiment, the vessel-like regions in the data set are first segmented and the skeleton of this segmentation is then found to make centerlines.

At each point, the measurement unit 25 takes a slice of the vessel on a plane that is substantially perpendicular to the centerline at that point, and measures at least one lumen diameter and at least one outer vessel diameter of the slice.

It may be appreciated that the vessel slice taken orthogonal to the centerline is unlikely to be perfectly circular. Therefore, for a given slice, any one of a choice of lumen diameters may be measured, for example a maximum diameter, a minimum diameter or any one of a number of intermediate diameters. The same applies to the outer vessel diameter. In this description, measuring a diameter may comprise combining two or more diameters (for example a minimum diameter and a maximum diameter) to obtain a further diameter, for example an average diameter.

In this embodiment, the measurement unit 25 measures the minimum lumen diameter and minimum outer vessel diameter of the slice. In most embodiments, the chosen measurement of the outer vessel diameter corresponds to the chosen measurement of the lumen diameter, for example both are minimum diameters, both are maximum diameters or both are average diameters.

In further embodiments, a different parameter of the slice is measured or calculated instead of or in addition to each diameter. The parameter may be a geometric parameter, for example a radius or a cross-section. Alternatively, the parameter may be any other parameter or summary statistic calculated using either or both of the inner contour region and the outer contour region.

In this embodiment, the measurement unit 25 passes values for the minimum lumen diameter and minimum outer vessel diameter at each point to the reference identification unit 26. The reference identification unit 26 then compares for each point the measured value of the minimum lumen diameter and the measured value of the minimum outer vessel diameter. In this embodiment, the reference identification unit 26 calculates for each point on the vessel a value for the atherosclerosis index (ASI).

The atherosclerosis index at a given point on the vessel may be defined as the minimum outer vessel diameter divided by the minimum lumen diameter.

A high ASI at a point indicates a likelihood of a vessel abnormality (for example, stenosis or aneurysm) at that point (although the assessment of this likelihood is refined through further stages in the process of FIG. 3). A low ASI at a point indicates that the vessel is likely to be healthy at this point, or at least is unlikely to have stenosis or aneurysm. Therefore the ASI may be used to divide the unbranched vessel section 74 into possible stenosis sections and reference sections, wherein the reference sections are sections of the unbranched vessel section 74 that are likely to be healthy.

In other embodiments, a different index or measure is calculated instead of or in addition to the atherosclerosis index. Other diameters may be used, for example maximum diameters or average diameters. Alternatively, radii or cross-sections may be used. The index or measure may be a ratio, or it may be any other appropriate combination of parameters.

At stage 46, the reference identification unit 26 divides the unbranched vessel section 74 into possible stenosis sections (non-reference sections) and reference sections based on the ASI at each of a plurality of points along the length of the vessel, using an ASI threshold. In this embodiment, the value of the ASI threshold is derived empirically. The reference identification unit 26 designates each point at which the ASI is above the threshold as a possible stenosis point, and designates each series of adjacent possible stenosis points as a possible stenosis section. The reference identification unit 26 then removes the possible stenosis section from the data set for the purposes of the next stage of the process. Removal of the section may be implemented by removing data from the data set, by not taking the relevant data into consideration in future steps, or by any suitable method. The reference identification unit 26 designates each remaining section of the unbranched vessel section as a reference section, and each point within each reference section as a reference point. The unbranched vessel section may comprise one or more reference sections and/or one or more possible stenosis sections. For the purposes of this description, it is assumed that the particular unbranched vessel section under discussion contains at least one reference section and at least one possible stenosis section.

In other embodiments, the reference identification unit 26 divides the unbranched vessel section 74 into possible stenosis sections and reference sections based on a different index or measure. In some of these embodiments, a threshold value for the index is applied. In further embodiments, the reference identification unit 26 may use alternative methods to distinguish reference sections from possible stenosis sections.

At stage 50, the calculation unit 28 calculates the expected lumen diameter for each possible stenosis point. This is the diameter that the vessel would be expected to have at that point if no stenosis or other abnormality were present. It is calculated by using the measured lumen diameters within one or more reference sections (the sections where it has been determined using the ASI index that there is unlikely to be stenosis present) to infer what the lumen diameters would have been within the possible stenosis sections if those sections had been stenosis-free.

The calculation unit 28 receives data from the reference identification unit 26, which comprises the definitions of the reference sections and possible stenosis sections that were defined in stage 48 and the measured lumen diameter at each point on the vessel.

In a first variant of this embodiment, the calculation unit 28 calculates expected lumen diameters in each possible stenosis section by using the measured lumen diameters at a plurality of points within an adjacent reference section. A regression line is fitted to the measured lumen diameters in the reference section, using any suitable method, for example, least squares, least median of squares or RANSAC (RANdom Sample Consensus). The regression line is then extrapolated over part or all of the possible stenosis section. The expected lumen diameter at each point in the possible stenosis section is the value of the extrapolated regression line that point.

In a second variant of the embodiment, each possible stenosis section has two adjacent reference sections, one at each end of the possible stenosis section. A regression line is fitted to the measured lumen diameters at a plurality of points within both of the reference sections, which is then interpolated at each point in the possible stenosis section. The expected lumen diameter at each point is the value of the interpolated regression line at that point.

The first and second embodiments may be combined if there is at least one possible stenosis section which is at the end of the unbranched vessel section and therefore has only one adjacent reference section, and at least one possible stenosis section which has two adjacent reference sections.

In a third variant of the embodiment, a single regression line is fitted to all of the measured lumen diameters at a plurality of points within all of the reference sections in the unbranched vessel section (which may equivalently be expressed as all points in the unbranched vessel section minus all the possible stenosis sections). The expected lumen diameter at any point in any possible stenosis section within the unbranched vessel section is the value of the single regression line at that point.

In alternative embodiments, a regression model or classifier is used instead of a regression line. In further embodiments, expected lumen diameters are calculated from the reference sections without use of a regression line, regression model or classifier. For example, in a simple model, the expected lumen diameter for each possible stenosis point is taken to be the measured lumen diameter at the nearest reference point to that possible stenosis point, or a combination of the measured lumen diameters at several nearby reference points.

For each possible stenosis point, the region identification unit 30 compares the expected lumen diameter to the lumen diameter that was measured in stage 48. In this embodiment, the region identification unit 30 calculates the measured-to-expected ratio (the measured lumen diameter divided by the expected lumen diameter). A value for the measured-to-expected ratio that is below 1 indicates that the vessel is narrower at that point than would be expected of a vessel without stenosis.

At stage 52, the region identification unit 30 uses the measured-to-expected ratio at each stenosis point to identify candidate stenosis regions. A ratio threshold is applied to each possible stenosis point. In this embodiment, the ratio threshold is 0.8. Any possible stenosis point having a measured-to-expected ratio less than 0.8 is designated a candidate stenosis point, and any series of adjacent candidate stenosis points is designated a candidate stenosis region.

The set of candidate stenosis points is a subset of the set of possible stenosis points of stage 48. Each possible stenosis point has an ASI (ratio of minimum outer vessel diameter to minimum lumen diameter) greater than the ASI threshold. Each candidate stenosis point has an ASI greater than the ASI threshold, and also has a measured-to-expected ratio less than the ratio threshold.

In this embodiment, the ratio threshold is a fixed setting within the region identification unit 30. In other embodiments, a different value for the ratio threshold is used. In further embodiments, the ratio threshold is provided by the user and may be dependent on the process or data type in the same manner as the ASI threshold above. In alternative embodiments, a different calculated parameter is used instead of the measured-to-expected ratio in designating candidate stenosis regions.

It may be expected that there will be sections of the vessel in which the value of the measured-to-expected ratio may dip just under or over the threshold for a short distance. Additionally, the calculation of the expected lumen diameters in stage 50 is expected to result in some noise. Therefore, it may be expected that in some cases, two candidate stenosis regions that are very close together ought to be considered as one stenosis region, the point or points between them being the result of a minor variation above the threshold, an artifact of calculation, or the result of noise.

The expected diameter may be based on a line regression and therefore may have a smooth profile without variations. However, the actual vessel segmentation, if set up to achieve more accuracy, would have small variations in the diameter. These small variations in the diameter may result in disjoint stenosis regions where there should be one combined stenosis region.

Similarly there may be a very short candidate stenosis region which is the result of an artifact or noise and should not be considered as a genuine stenosis region. It may be expected that a genuine stenosis would meet some minimum physical extent.

Therefore in stage 54, the region identification unit 30 filters and merges the candidate stenosis regions to obtain final stenosis regions. The aim of this process is to remove the effects of artifacts and noise as described above.

In this embodiment, if a candidate stenosis region is very small (less than 0.5 mm in length) the region identification unit 30 disregards this candidate stenosis and does not identify it as a final stenosis region. If two neighboring candidate stenosis regions are separated by a very short distance (less than 0.5 mm) then the region identification unit 30 merges the two candidate stenosis regions into a single final stenosis region. In different embodiments, the sizes of the allowed lengths or separations may vary.

In further embodiments, the region identification unit 30 performs a filtering and merging process in dependence not only on the length or separation of candidate stenosis regions, but in dependence also on the value of the measured-to-expected ratio for the points within these regions, or any other suitable size and composition heuristics. For example, a possible stenosis point with a measured-to-expected ratio just above the threshold may be more likely to be merged with one or more adjacent candidate stenosis regions than one with a ratio close to one (no narrowing, measured lumen diameter equal to expected lumen diameter). Alternatively, single points with large differences in measured-to-expected ratio from their adjacent points may be considered more likely to be artifacts than those with smaller differences.

In alternative embodiments, no filtering and merging process is carried out and the region identification unit 30 designates the candidate stenosis regions as final stenosis regions for stage 56 onwards.

In the present embodiment, the process of FIG. 3 proceeds to stage 56 after the completion of stage 54. However, some embodiments comprise an iterative region refinement process that is represented by the dotted line in FIG. 3. In the iterative region refinement process, the final stenosis regions defined in stage 54 are used as an input for a repeat of stage 48, where stage 48 is the division of the unbranched vessel section into possible stenosis sections and reference sections. The reference identification unit 26 defines the possible stenosis sections as being the final stenosis regions of stage 54, rather than defining them using the ASI as was done on the first pass through stage 48. The reference identification unit 26 then removes these revised possible stenosis sections from the unbranched vessel section and designates the remaining sections as reference sections. Stages 50, 52 and 54 are repeated on these newly-defined reference sections and possible stenosis sections, resulting in a new set of final stenosis regions. At this point the process may proceed to stage 56, or another iteration of the regions may be carried out by once again following the dotted arrow to stage 48. This iterative procedure may result in more accurate definition of the final stenosis regions.

Each unbranched vessel section may comprise one or more final stenosis regions (or may comprise no final stenosis regions if no stenosis is present in that vessel section). At stage 56, the region identification unit 30 finds the maximum stenosis point in each of the final stenosis regions. The maximum stenosis point of a final stenosis region is defined as the point at which the narrowing of the vessel is greatest. In one embodiment, this is determined by taking the point within the final stenosis region at which the measured lumen diameter is smallest. In another embodiment, it is determined by taking the point within the final stenosis region at which the value of the measured to-expected ratio is lowest. In further embodiments, it is determined in dependence on the gradient or rate of change of lumen diameter or measured-to-expected ratio along the length of the final stenosis region or by any other suitable method.

At stage 58, the region identification unit 30 quantifies the severity of the stenosis at the maximum stenosis point. In this embodiment, the severity of the stenosis is quantified by calculating a percentage stenosis at the maximum stenosis point. The percentage stenosis is calculated by comparing the measured lumen diameter at the maximum stenosis point to the measured lumen diameter at a proximal reference point. In this embodiment, the proximal reference point is the nearest reference point in the unbranched vessel section, where the distance to the reference point is measured along the center line of the vessel. If two reference points are equally close to the maximum stenosis point, the region identification unit 30 may choose between them when calculating the percentage stenosis, or may average the lumen diameters at the two reference points. In further embodiments, a different definition of the proximal reference point may be used or the measured lumen diameter at several reference points may be combined to give a combined lumen diameter.

In this embodiment, percentage stenosis is calculated using Equation 1:

$$\text{Percent} = \frac{D_{ref} - D_{msp}}{D_{ref}} \times 100\% \quad \text{(Equation 1)}$$

where Percent is the percentage stenosis, $D_{ref}$ is the measured lumen diameter at the reference point, and $D_{map}$ is the measured lumen diameter at the maximum stenosis point. This is analogous to a method that may be used in clinical practice, in which a clinician calculates percentage stenosis from an image by measuring the lumen diameter on the image at the point of maximum stenosis, measuring the lumen diameter at the nearest healthy point on the vessel, and using Equation 1 above.

In alternative embodiments, any suitable quantity may be used to quantify the severity of the stenosis, including any calculation of the percentage stenosis, or of the size of the lumen diameter itself (where the vessels are of approximately constant diameter, the most severe stenosis may simply be the narrowest vessel).

Although the description of the embodiments above has been expressed in terms of lumen diameter (and, in particular, minimum lumen diameter) throughout, further embodiments use lumen radius or lumen cross-section to calculate a percentage stenosis or other suitable measure of severity of stenosis.

The region identification unit 30 calculates the percentage stenosis at the maximum stenosis point for each of the final stenosis regions in each of the unbranched vessel sections. For each final stenosis region, the percentage stenosis for the maximum stenosis point within the final stenosis region may also be called the percentage stenosis for the final stenosis region. In this embodiment, there is no averaging or combining of the percentage stenosis values along the length of a stenosis region, and the percentage stenosis at the maximum stenosis point is taken to be the percentage stenosis value that is associated with the stenosis region as a whole.

In a further embodiment, the region identification unit 30 calculates data for all of the stenosis regions in the coronary vessel tree and uses segment information to provide a standard per-segment QCA (quantitative coronary angiography) analysis. The percentage stenosis may be provided for each of the 17 AHA (American Heart Association) segments of the coronary vessel tree. A stenosis grade (mild, moderate, severe, occluded) may be assigned for each stenosis.

At stage 60, the display generation unit 32 displays an image in which some or all of the final stenosis regions are indicated by applying a visual effect to the image. The visual effect is intended to draw the user's interest to the regions on which it is used, thus saving time and effort when compared with manual identification of stenosis. In this embodiment, whether a given final stenosis region is indicated by the visual effect depends on whether the percentage stenosis of that final stenosis region meets a display threshold.

The display generation unit 32 receives from the region identification unit 30 data on each final stenosis region, including the position and extent of the final stenosis region and the percentage stenosis at the maximum stenosis point. The display generation unit 32 receives the original set of volumetric image data or the segmented set of volumetric image data in which the vessels have been isolated from the segmentation unit 24, the memory 20 or data store. Alternatively, it receives the set of image data or segmented set of image data from any other unit or part of the apparatus.

The display generation unit 32 generates an image from the received set of image data that represents at least one of the final stenosis regions that has been identified by the region identification unit 30. The image comprises any view suitable for the display of CT angiography image data, for example an SVR (Shaded Volume Rendering) view. The image is displayed on display screen 16.

In this embodiment, the display threshold is 50%. Each final stenosis region for which the percentage stenosis is 50% or over is highlighted in the image by applying a color, for example red, to the final stenosis region, in order to draw the clinician's attention. The same color is applied to each final stenosis region for which the percentage stenosis is 50% or over. Each final stenosis region for which the percentage stenosis is below 50% is not highlighted and is displayed in the same manner as any other non-highlighted part of the image.

In other embodiments, the display threshold is set to a different value, for example 30% stenosis or 70% stenosis. In further embodiments, multiple display thresholds are set, having different values for the percentage stenosis. In one embodiment, a first display threshold is set at 50% stenosis and a second display threshold is set at 70% stenosis. All final stenosis regions for which the percentage stenosis value is 50% or more are highlighted in the final image, but those having a display threshold of 70% or more are highlighted in a different color from those that have a percentage stenosis between 50% and 70%. In alternative embodiments, all final stenosis regions are highlighted, with no percentage stenosis thresholding.

A display threshold may be set as a system parameter or it may be input by a user. The user may provide an overall threshold to be applied to every generated image, or to images of a particular type. Alternatively, the user may provide a threshold that is specific to a particular image. In one embodiment, after display of an image using the system threshold (for example 50%) the user may select a further display threshold (for example 70%) and redisplay the image with the new threshold applied.

In the present embodiment, the highlighting of the final stenosis regions comprises applying a color to the image. In further embodiments, each final stenosis region that the display generation unit 32 selects for highlighting is highlighted in a manner other than by applying a color, for example by using an altered intensity value, applying a halo, drawing an arrow or circle or other indicator onto the image, or any other modification to the image that may indicate a final stenosis region. In still further embodiments, the display generation unit 32 adds a numerical or text display to the screen, denoting the percentage stenosis at one or more maximum stenosis points (for example, giving a percentage stenosis beside each highlighted final stenosis section, or displaying the highest percentage stenosis that is found within the image).

In still further embodiments, the display threshold is replaced or supplemented by a color gradient or intensity gradient that is applied in dependence on the percentage stenosis. For example, the color in which each final stenosis region is highlighted is selected from a color scale in which 0% stenosis is represented in blue, 100% stenosis in red, and intermediate values of percentage stenosis in the corresponding intermediate color between blue and red on a predetermined color scale.

In all of the embodiments above, the percentage stenosis value for a final stenosis region is the percentage stenosis at the maximum stenosis point of that final stenosis region. However, in alternative embodiments, a percentage stenosis is calculated for each point within a final stenosis, by comparing the measured lumen diameter at that point to the measured lumen diameter at the nearest reference point, using Equation 1 but substituting the diameter at the final stenosis point in question for the diameter at the maximum stenosis point. The display generation unit 32 then applies one or more thresholds, color scales or other methods of highlighting as described above, but on a per-point basis rather than per-region. This may result in stepped or graduated color along each final stenosis region, in dependence on the percentage stenosis at each point.

Although the embodiments above describe highlighting and thresholding based on the percentage stenosis as defined in Equation 1, in further embodiments any suitable quantity that may quantify the severity of stenosis may be used, for example the measured-to-expected ratio itself.

In addition to the automatic calculation of percentage stenosis outlined above, the clinician may also perform manual measurements on the resulting image if desired, using standard methods.

In other embodiments, similar methods are used to assess, quantify and display the extent of stenosis in other vessels of the body, including but not limited to arteries, veins, carotid arteries and renal arteries.

Whilst particular units have been described herein, in alternative embodiments functionality of one or more of these units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus for processing volumetric image data to identify vessel regions having a predetermined condition, comprising:
 a computer processor configured to:
  receive the volumetric image data;
  remove at least one branch region from the volumetric image data to obtain data representing a branch-free vessel;
  measure a vessel lumen parameter and an outer vessel parameter at each of a plurality of points on the branch-free vessel;
  identify at least one reference section of the branch-free vessel and at least one non-reference section of the branch-free vessel;
  wherein the identifying of the at least one reference section and the identifying of the at least one non-reference section is based on the measurements of the vessel lumen parameter and the outer vessel parameter for the plurality of points on the branch-free vessel;
  for each non-reference section of the branch-free vessel, calculate an expected value of the vessel lumen parameter in the non-reference section of the branch-free vessel based on at least one measured value of the vessel lumen parameter in the at least one reference section;

for at least one non-reference section of the branch-free vessel, identify the non-reference section of the vessel as a candidate stenosis region in dependence on both the expected value of the vessel lumen parameter in the non-reference section and a measured value of the vessel lumen parameter in the non-reference section;

perform an iterative procedure to refine identification of the at least one reference section and the at least one non-reference section based on the candidate stenosis region or regions, and to refine identification of the candidate stenosis region or regions based on the refined at least one reference section and the at least one non-reference section to generate at least one final stenosis region;

within each final stenosis region, identify a maximum stenosis point, and quantify stenosis for each maximum stenosis point; and display with a highlighting each final stenosis region with a stenosis greater than a predetermined threshold.

2. An apparatus according to claim 1, wherein the volumetric image data represents a vessel tree comprising at least one vessel branch, and the computer processor obtains the branch-free vessel by operations including:

defining the at least one branch region, wherein the or each branch region corresponds to a respective branch point; and removing the at least one branch region from the set of volumetric image data.

3. An apparatus according to claim 2 wherein the at least one branch region is defined by applying a branch length threshold.

4. An apparatus according to claim 1 wherein the computer processor is further configured to compare the expected value of the vessel lumen parameter to the measured value of the vessel lumen parameter and to identify the region of candidate stenosis region or regions based on the comparison.

5. An apparatus according to claim 4, wherein the comparing the expected value of the vessel lumen parameter to the measured value of the vessel lumen parameter comprises calculating a measured-to-expected ratio.

6. An apparatus according to claim 1 wherein the vessel lumen parameter and outer vessel parameter comprise a measure of lumen size, and the computer processor identifies the at least one reference section by operations including:

identifying the at least one non-reference section based on a comparison between a measured value of the lumen size and a measured value of vessel size; and identifying at least one remaining vessel section as the reference section.

7. An apparatus according to claim 1 wherein the computer processor is further configured to calculate atherosclerosis index (ASI) values for a plurality of points along the vessel, and to identify the reference section in dependence on the calculated ASI values.

8. An apparatus according to claim 1 wherein the computer processor is further configured to determine the candidate stenosis region or regions based on a comparison between a value based on the vessel lumen parameter and the outer vessel parameter in the candidate stenosis region or regions and a value based on the vessel lumen parameter and the outer vessel parameter in the reference section.

9. An apparatus according to claim 8, wherein the computer processor quantifies stenosis within each final stenosis region by:

comparing the measured value of the parameter at the maximum stenosis point to the value of the vessel lumen parameter and the outer vessel parameter at a proximal reference point.

10. An apparatus according to claim 1, wherein the computer processor calculates an expected value of the vessel lumen parameter and outer vessel parameter for the non-reference section of the vessel by operations including:

measuring a value of the vessel lumen parameter and outer vessel parameter at each of a plurality of points within the at least one reference section;

fitting a function to the plurality of measured values;

interpolating or extrapolating the fitted function to at least one point within the non-reference section.

11. An apparatus according to claim 10 wherein the function comprises at least one of: a regression line, a regression model, a classifier.

12. An apparatus according to claim 1 wherein the computer processor measures the value of the vessel lumen parameter and outer vessel parameter in a section by an operation including measuring the value of the vessel lumen parameter and outer vessel parameter at at least one point within the section, and by operations including:

determining a center line of the vessel at the point; and measuring the value of the vessel lumen parameter and outer vessel parameter on a plane that is substantially perpendicular to the center line of the vessel at the point.

13. An apparatus according to claim 1 wherein the vessel lumen parameter and outer vessel parameter comprise at least one of: a lumen diameter, a lumen radius, a lumen cross-section.

14. An apparatus according to claim 1, wherein the computer processor is further configured to identify the at least one reference section in dependence on a comparison between at least one value of the vessel lumen parameter and outer vessel parameter and at least one measured value of a further parameter.

15. An apparatus according to claim 14, wherein the further parameter comprises at least one of a vessel diameter, a vessel radius, a vessel cross-section, a vessel size parameter, a vessel shape parameter.

16. An apparatus according to claim 1 further comprising a display to display an image representing the at least one final stenosis region.

17. An apparatus according to claim 16 wherein the highlighting is applied to the image in dependence on an amount of the stenosis being greater than the predetermined threshold.

18. An apparatus according to claim 1 wherein the vessel comprises at least one of: an artery, a vein, a coronary artery, a renal artery, a carotid artery.

19. An apparatus according to claim 1, wherein to generate the at least one final stenosis region, the computer processor is further configured to at least one of filter and merge the identified candidate stenosis region or regions.

20. A method for automatic detection of vessel regions having a condition, comprising:

receiving volumetric image data;

removing at least one branch region from the volumetric image data to obtain data representing a branch-free vessel;

measuring a vessel lumen parameter and an outer vessel parameter at each of a plurality of points on the branch-free vessel;

identifying at least one reference section of the branch-free vessel and at least one non-reference section of the branch-free vessel;

wherein the identifying of the at least one reference section and the identifying of the at least one non-reference section is based on the measurements of the vessel lumen parameter and the outer vessel parameter for the plurality of points on the branch-free vessel;

for each non-reference section of the branch-free vessel, calculating an expected value of the vessel lumen parameter in the non-reference section of the vessel based on the at least one measured value of the vessel lumen parameter for the at least one reference section; and for at least one non-reference section of the branch-free vessel, identifying the non-reference section of the vessel as a candidate stenosis region in dependence on both the expected value of the vessel lumen parameter in the non-reference section and the measured value of the vessel lumen parameter in the non-reference section;

performing an iterative procedure to refine identification of the at least one reference section and at least one non-reference section based on the candidate stenosis region or regions, and to refine identification of the candidate stenosis region or regions based on the refined at least one reference section and at least one non-reference section to generate at least one final stenosis region;

within each final stenosis region, identifying a maximum stenosis point, and quantifying stenosis for each maximum stenosis point; and displaying with a highlighting any candidate stenosis region with a stenosis greater than a predetermined threshold.

21. A non-transitory computer readable memory storing computer-readable instructions that are executable to perform a method according to claim 20.

* * * * *